United States Patent [19]

Greer et al.

[11] Patent Number: 5,437,882
[45] Date of Patent: Aug. 1, 1995

[54] CONTROLLER FOR A FEED GRAIN CONDITIONER

[75] Inventors: Bryan D. Greer, Anoka, Minn.; David M. Mills, Crossnore, N.C.

[73] Assignee: BioChem, Inc., Cambridge, Minn.

[21] Appl. No.: 276,351

[22] Filed: Jul. 18, 1994

[51] Int. Cl.⁶ .................. A23L 1/00; A23N 17/00; G01N 33/00
[52] U.S. Cl. .................. 426/231; 99/487; 99/516; 99/536; 364/469; 426/507
[58] Field of Search ............... 426/231, 506, 507, 455; 99/485, 486, 487, 488, 516, 534, 536; 364/468, 469

[56] References Cited

U.S. PATENT DOCUMENTS

| 4,829,891 | 5/1989 | Satake | 99/471 |
| 5,133,982 | 7/1992 | Bodkin et al. | 99/487 |
| 5,194,275 | 3/1993 | Greer | 426/231 |

*Primary Examiner*—George Yeung
*Attorney, Agent, or Firm*—Burd, Bartz & Gutenkauf

[57] ABSTRACT

An improved controller for a feed grain conditioning device is characterized by a microcontroller which operates valve actuator relays to control the delivery of moisture to feed grains in order to adjust the grain moisture content to a desired level. A software program controls the operation of the microcontroller. It includes a main program affording user interface and an interrupt program used to calculate the moisture flow necessary to attain the target moisture content in accordance with the moisture content of untreated grain and with the grain mass flow.

10 Claims, 3 Drawing Sheets

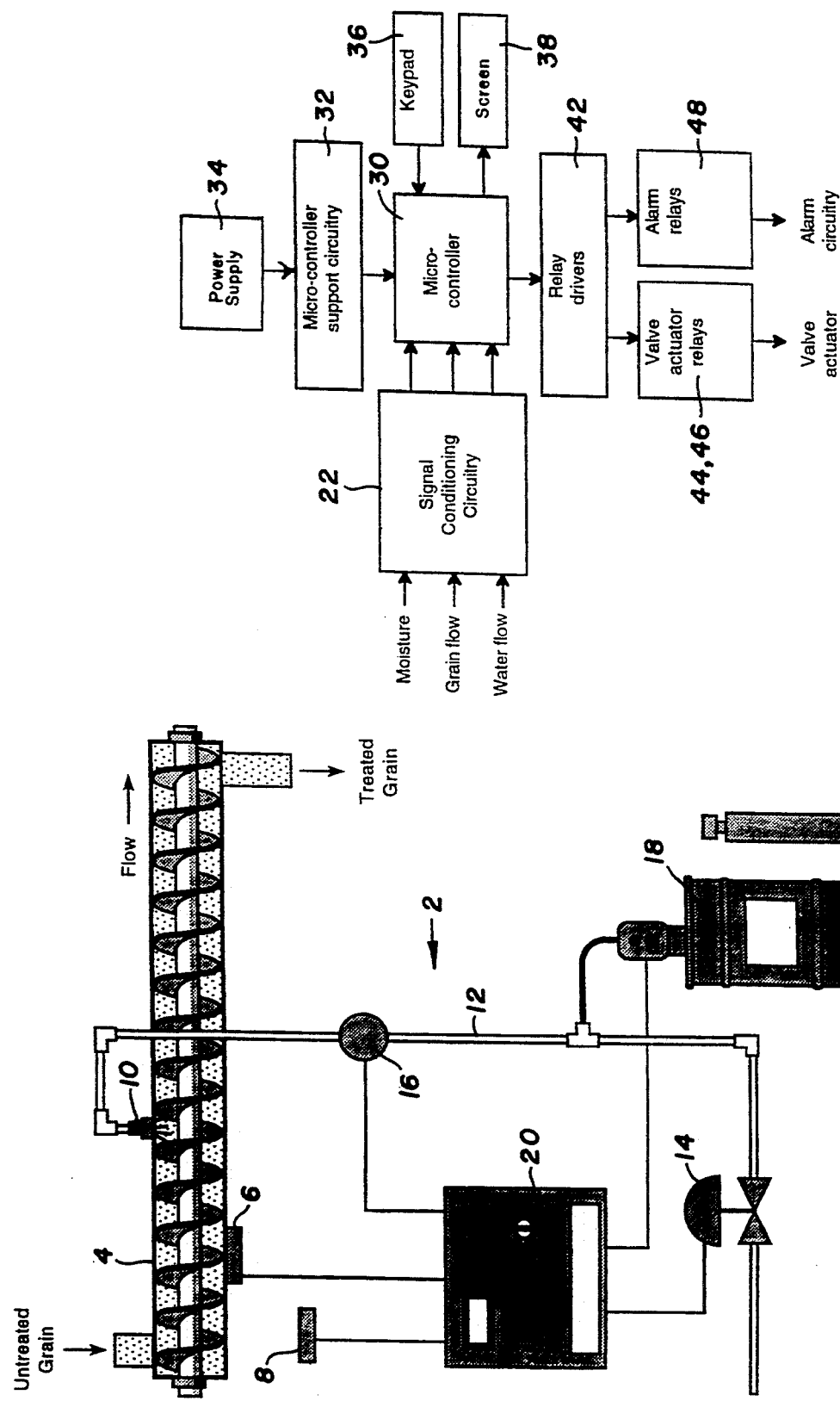

5,437,882

CONTROLLER FOR A FEED GRAIN CONDITIONER

BACKGROUND OF THE INVENTION

Feed grains used to manufacture commercial livestock feed can vary a great deal in moisture content. Depending on the time of the year and grain type, the moisture content can be as low as eight percent or as high as eighteen percent. This variation has a very significant effect on such parameters as particle size and particle size distribution of the grain in the finished feed, degree of cooking as measured by starch gelatinization, energy density of the feed, and palatability.

In any manufacturing process, the more uniform the incoming materials, the more uniform the finished product. Having moisture as an uncontrolled variable in the feed manufacturing process introduces significant variations in the processing efficiency and finished product quality. Therefore it is highly desirable that all of the grain be of a constant moisture content.

BRIEF DESCRIPTION OF THE PRIOR ART

Devices for adding moisture to feed grain to increase the moisture content thereof to a target level are known in the patented prior art. U.S. Pat. No. 5,194,275, which is commonly owned with the present invention, discloses a feed grain conditioner for adjusting the moisture content of grain being transferred through an auger. A capacitive moisture sensor is mounted on the auger and produces an output signal proportional to the moisture level of the untreated grain, and a load sensor is provided to produce an output indicative of the quantity of the grain. A control unit analyzes the signals and determines the necessary moisture flow to be supplied to the grain to bring its moisture content to the target level. More particularly, a flow meter provides a signal corresponding with the actual flow of moisture in a moisture supply line, and the control unit adjusts a valve in the supply line until the actual flow corresponds with the calculated flow.

While the prior device operates satisfactorily, there are limits to the accuracy and versatility of the control unit. The present invention was developed in order to overcome these drawbacks by providing an improved method and device for controlling the delivery of moisture to grain within a grain conditioning device so that all of the conditioned grain will have the same moisture content.

SUMMARY OF THE INVENTION

Accordingly, it is a primary object of the invention to provide an improved controller and method for adjusting the moisture content of feed grains to a given level in a feed conditioner. The controller includes a microcontroller which receives input signals corresponding with the moisture content of untreated grains, grain flow, and moisture flow and processes these signals to produce output control signals. A relay driver circuit is connected with the microcontroller for receiving the output control signals and for producing at least one complementary pair of actuating signals. A relay is connected with the relay driver circuit and is operable to open and close a moisture flow control valve in response to the complementary actuating signals, respectively, to control the delivery of moisture from the conditioner to the grain in accordance with the input signals.

One or more alarm relays are also connected with the relay driver circuit to produce alarm signals when grain moisture levels and grain flow rates are above and below predetermined ranges. An alarm signal is also produced to indicate differences between calculated and actual moisture flows.

In order to provide an interface between the user and the controller, a keypad and a display are connected with the microcontroller. The keypad is used to operate the controller by initiating various processing sequences and for calling up certain parameters of the conditioning operation which are displayed on the screen.

Signals corresponding to the sensed moisture content, grain mass flow, and moisture flow can be integrated to produce outputs corresponding to the average and total grain and moisture flows and to the average moisture content of the untreated grain.

BRIEF DESCRIPTION OF THE FIGURES

Other object and advantages of the invention will become apparent from a study of the following specification when viewed in the light of the accompanying drawing in which:

FIG. 1 is a schematic view of a feed grain conditioning apparatus according to the prior art;

FIG. 2 is a block diagram of the improved controller for a feed grain conditioner according to the invention;

DETAILED DESCRIPTION

Figure 3:
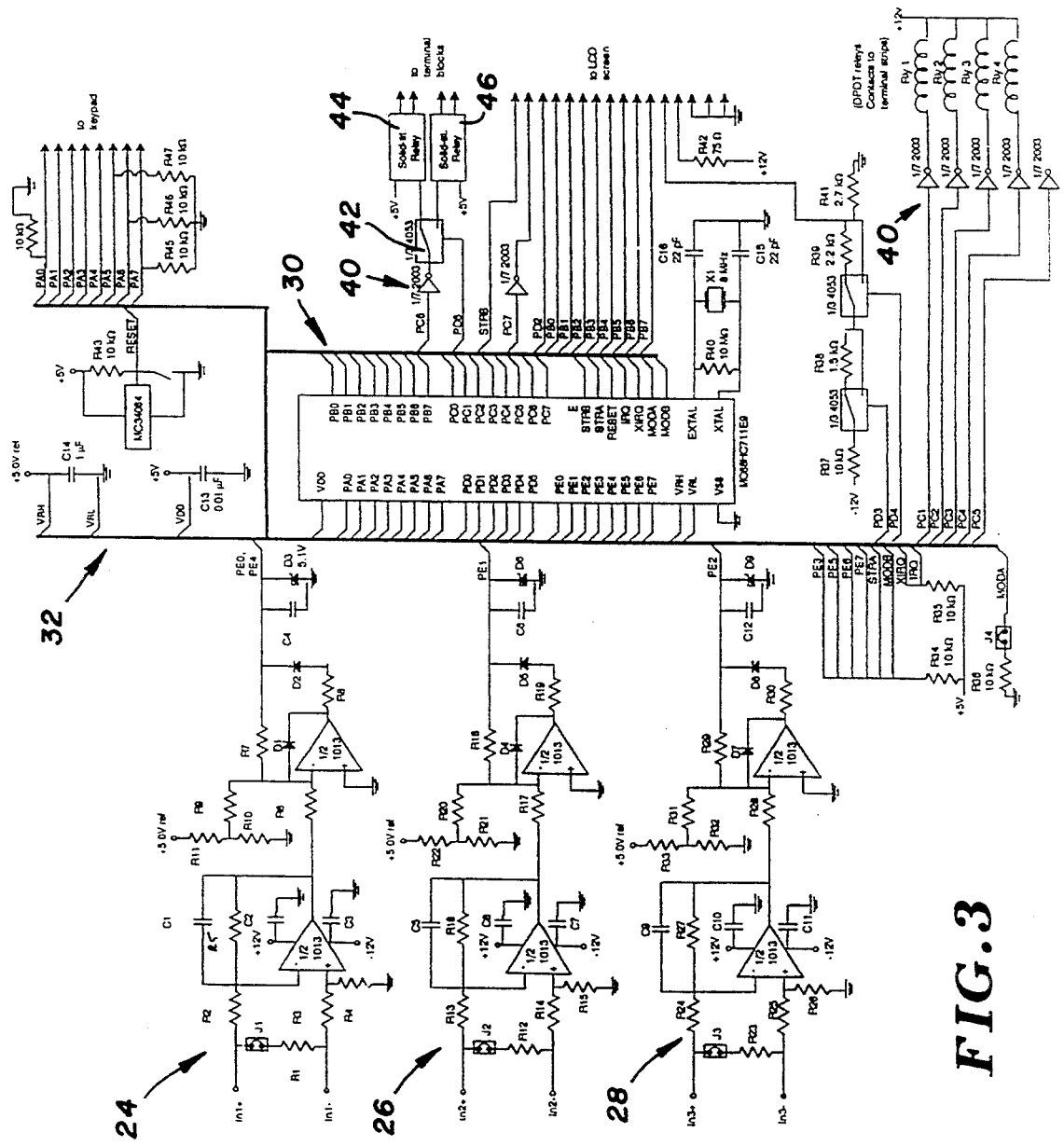
FIG. 3 is a circuit diagram of the controller of FIG. 2.

Referring first to FIG. 1, a feed grain processor 2 of the prior art such as that disclosed in U.S. Pat. No. 5,194,275 will be described. Untreated grain such as corn, barley, oats, wheat or the like is transported through an auger 4 in which the grain is mixed with moisture such as water or a mixture of water and a wetting agent. A capacitive moisture sensor 6 is mounted on the auger for measuring the moisture content of the untreated grain supplied to the auger. A load sensor 8 is connected with an elevator motor and provides an output signal corresponding with the grain mass flow rate. A spray nozzle 10 is connected with the auger for supplying moisture to the grain being transported therethrough. Water is delivered to the spray nozzle via a water supply line 12, and the water flow is controlled by a valve 14. A sensor 16 is connected with the line 12 to provide an output signal corresponding with the moisture flow. A wetting agent can be added to the water from a storage tank 18 to enhance the absorption of the moisture by the grain. A control unit 20 determines the water flow necessary to adjust the moisture content of the grain to a target level based on the mass of the grain and the moisture content of the untreated grain. The control unit adjusts the control valve 14 until the actual flow of the water matches the calculated flow.

The improved controller of the present invention will be described with reference to FIGS. 2 and 3. It receives the same input signals as that of the controller of FIG. 1, namely analog signals related to untreated grain moisture content, grain flow, and actual water flow. These inputs are delivered to a signal conditioning circuitry 22 which as shown in FIG. 3 comprises three circuits 24, 26, 28, one for each analog input signal.

Since the conditioning circuits 24,26,28 shown in FIG. 3 are the same, only the circuit 24 will be described. A differential voltage input is connected to points In1+ and In1− at the left side of the circuit diagram with J1 open-circuited. If a current input is to be used, a jumper placed over J1 allows the current to flow through R1, creating a differential voltage across In1+ and In1−. Matched resistors R2,R3,R4, and R5 form an inverting difference amplifier with op-amp U1, and capacitor C1 filters the signal with a cutoff frequency of about 5 Hz. Large resistances are used to minimize input leakage current.

The second op-amp circuit functions as an inverting, summing amplifier (adding in a voltage offset) and prevents the signal from exceeding the range of 0 to 5.1 V. The 5.0 V reference voltage appears across the voltage divider network of R11 and R10. R11 is one resistor of a socketed resistor network which may be changed to adjust the amount of voltage offset. This voltage is then summed with the inverted signal voltage and inverted again through the inverting amplifier comprised of the op-amp, R7, and R6. R7 is also a socketed resistor network which may be changed to compensate for varying signal ranges. In this way, a wide variety of input signal ranges may be converted into approximately the 0–5 V range required by the microcontroller's analog-to-digital converter. Resistor networks were used instead of potentiometers for reasons of stability and reliability.

Diodes D1 and D2 prevent the microprocessor input from falling below ground. Diode D3, a 5.1 V zener diode, clips the signal at 5.1 V, and when the signal is clipped, R8 limits current through the diode. C4 filters any high-frequency noise from the signal.

The input signals from the signal conditioning circuitry 22 are delivered to a microcontroller 30. A suitable microcontroller is a Motorola model MC68HC711E9 which incorporates analog inputs, digital inputs and outputs, program memory, non-volatile parameter memory, and a random access memory in a single chip. The microcontroller is supported by circuitry 32 comprising the basic hardware needed for its operation, including a crystal oscillator, a low power reset, and power-supply filtering circuitry shown in FIG. 3.

A ±12 V power supply 34 is connected with the controller via the support circuitry and generates a 5 V supply for the microcontroller logic circuitry as well as a 5 V reference voltage used on the signal conditioning circuitry 22 and for analog-to-digital conversion.

The microcontroller 30 is used in a single chip mode running at a clock frequency of 2 MHz. It has numerous ports comprising various input and output pins that can be utilized for controlling and monitoring various devices.

Figure 4:
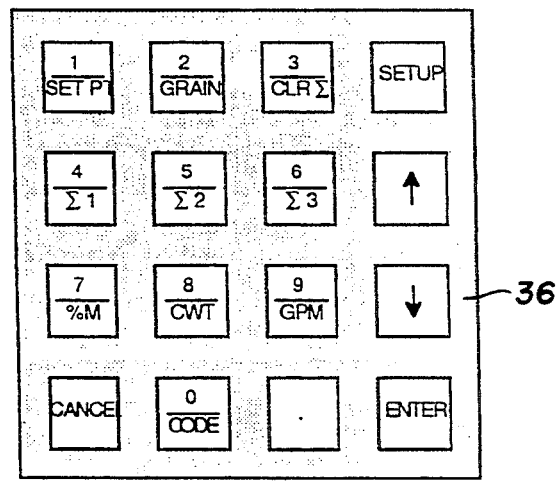
FIG. 4 is a plan view of the keypad for interfacing with the controller of FIG. 2.

A 16 key (4×4 matrix) keypad 36 is connected with the microcontroller to allow user input, direct numerical entry, menu selection, and a variety of other specific functions. The keypad is shown in detail in FIG. 4. Connection with the microcontroller is made at port A which in the example shown includes four input pins and four output pins (FIG. 3). With a 4×4 matrix keypad, the microcontroller places a signal at each column while scanning each row to see if a key has been pressed. Thus, the four output pins are connected to the four columns and the four input pins are connected to ground through a 10 kΩ resistor network and then to the four rows of the keypad. With this arrangement, the user can input data directly into the microcontroller 30 in order to vary control parameters and perform other operations.

The key layout on the keypad 36 indicates to the user what each key represents: 1 to edit set point, 2 to select grain type, 3 to clear sums/averages, 4–6 to display sums/averages for each grain type, 7 to fix a manual incoming moisture level, 8 to do the same for grain flow, 9 to enter a manual output water flow, and 0 to enter a security code to access set up parameters.

In order for the user to receive feedback from the microcontroller to monitor the system, an LCD display screen 38 with variable contrast is connected with the microcontroller. It provides a display of operating conditions, setup parameters, menus, and the like. In order to connect the screen with the microcontroller, several lines are required including data lines, strobe lines, and power. Port B of the microcontroller was selected for the data lines between the microcontroller and the screen as shown in FIG. 3. The strobe line STRB is needed to signal the screen when data is valid at port B. A read/write line from the screen is connected to ground so that data is always written to the screen. The register select (RS) line is connected to an output pin so that either data or addresses could be written to the screen. Thus, any location on the screen can be located through addressing.

If the proper security code has been entered in the security screen, pressing the setup key on the keypad accesses the menu for system set-up. There are two screens of set-up menu, and the second may be accessed by pressing either a down arrow or the setup key again from the first set-up menu screen. The set-up screens display a menu consisting of a list of numbers and set-up parameter categories. Pressing the number for a listed category brings up the first screen in that category. The rest of the screens may be accessed from these with the up and down arrow keys. Each set-up screen may contain either numbers to edit or text to edit. Every line with editable parameters has a number. Pressing that number key allows the user to edit the corresponding parameter.

Numbers are entered by typing the number directly and pressing enter. The program automatically leaves edit mode when enter is pressed. If a mistake is made, pressing cancel resets the number to its former state and exits edit mode. Text is edited differently. Any editable text is some sort of a list, such as Yes/No or a list of five grain types. The user edits these by cycling through the options with the up and down arrow keys. When the desired value is displayed, pressing enter will cause the program to save the value and exit edit mode. Again, cancel restores the previous value and exits edit mode.

When not in edit mode, cancel returns the display to the menu above it in the screen menu hierarchy. Cancel pressed from a setup menu returns the program to the operating screen. Setup brings up the first setup menu from any screen.

From the inputs relating to moisture content and mass flow of untreated grain, the microcontroller calculates the moisture required to be supplied to the grain to adjust the grain moisture content to a target level. By sensing the actual moisture flow, and comparing it with the calculated flow, the microcontroller produces complementary output signals which open or close the flow control valve to increase or decrease the actual moisture flow until it coincides with the calculated flow.

The complementary output signals should be 110 VAC signals which turn on and off small AC motors which operate the valve. The steady-state current required by these motors is less than 0.5 A so small wires can be used to run these signals. Since these signals must be 110 VAC, AC output modules are used to provide the levels necessary. In order to use these devices, a TTL or 5 V signal is used to control the high voltage side of the module. Isolation is built into the device in order to eliminate the need for external circuitry. However, they require more current than can be safely provided from the microcontroller. Therefore, an output buffer of some sort is required. Also, since there is both a clockwise and a counterclockwise motor, it is required that both motors never be on at the same time. A switch (SPDT) provides the necessary complementary operation since either one or the other terminal of the switch is connected, but not both. Thus, an analog multiplexer 40 is used as the device required for this operation. An output pin of a relay driver 42 is used as the input to the switch, as will be discussed below. The multiplexer switches between two solid state relays 44, 46 to control the valve motors as shown in FIG. 3.

Output pin B6 of the microcontroller is connected to one of the relay drivers, which is in turn connected to the analog multiplexer. The control line of the multiplexer is connected to output pin D2, and the output is then connected to the output modules. In this way, the actuator can be controlled as required by the present conditions.

The microcontroller also operates a plurality of alarms to indicate when certain signals are above or below a predetermined range. The alarms preferably comprise relays 48 so that they are capable of driving external alarm devices that run off of 110 VAC up to 5 A. Suitable relays comprise DPDT relays (FIG. 3) since both lines should be switched when controlling AC. However, the microcontroller cannot directly drive relays since up to 100 mA is required to drive standard mechanical relays. Accordingly, the relay driver 42 is provided for all of the alarm relays.

Connection of the relay driver to the microcontroller is done via pins 1-7 of Port C. This port is used due to the fact that it can be an output port. Then, the four relays are connected to the lower four bits of the output of the relay driver. When this device is activated with a high on one of the input lines, the output sinks current through the device and allows current to flow through an external device. The relays are connected to the supply voltage and then to the relay drivers in order to cause the relays to be activated according to the signals on Port C.

Figure 5:
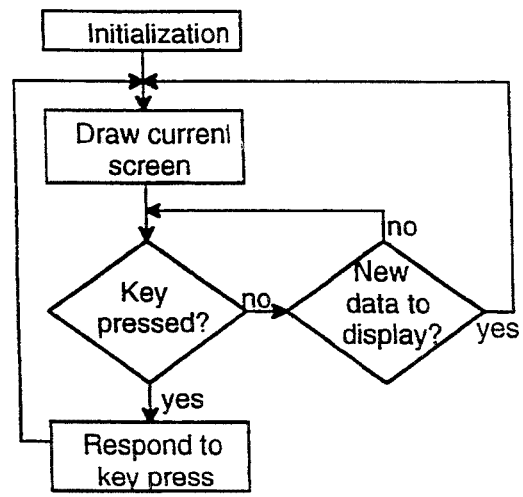
FIG. 5 is a flow chart of the main program for controlling the operation of the controller of FIG. 2.
Figure 6:
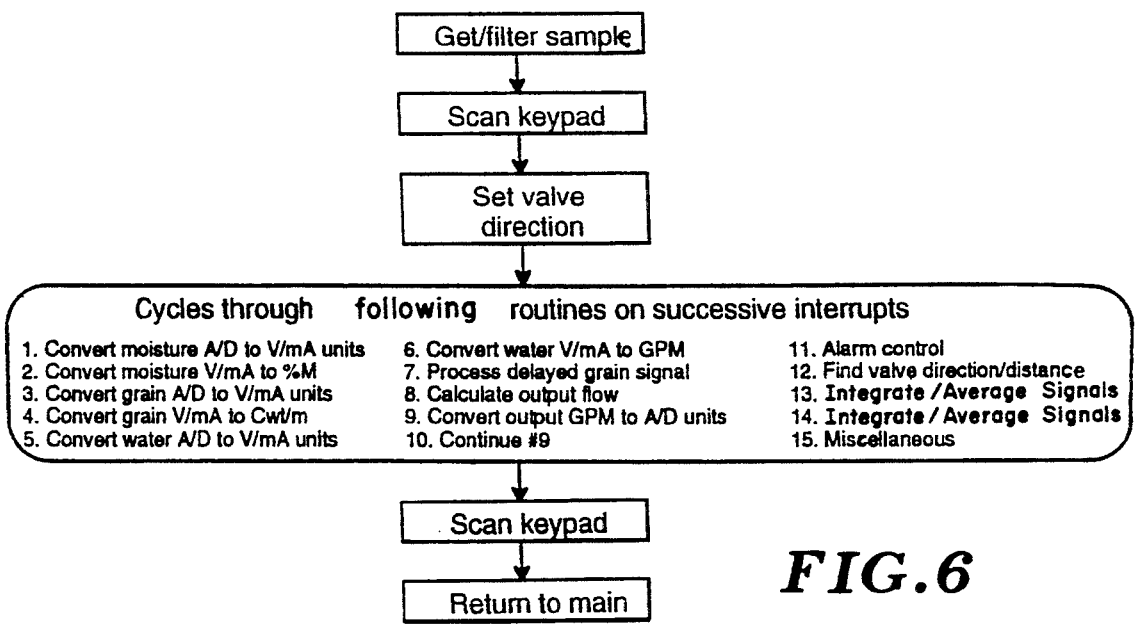
FIG. 6 is a flow chart of the interrupt program for controlling the operation of the controller of FIG. 2.

Referring now to FIGS. 5 and 6, the controller software will be described. The software comprises a main program (FIG. 5) which waits for keys to be pressed on the keypad by the user and responds accordingly, and an interrupt program (FIG. 6) which is entered automatically every 32.8 ms and handles signal processing and keypad scanning.

The first step in the main program is initialization. During initialization, the microcontroller configures all of its inputs and outputs. As necessary, program variables are loaded with initial values. The screen is initialized and custom characters are loaded into screen memory.

Next, the program enters its main program loop, which consists of the following instructions: (1) draw the current screen; (2) wait for an input and process it; and (3) repeat. While this loop is being executed, an interrupt occurs every 32.8 ms.

The term "screen" is used to mean a set of information displayed on the LCD screen at one time. More than thirty different screens are provided for all user information display, setup parameters, and menus. Screens are stored in a specific data format. The first data structure is a set of four pointers which point to screen information, screen menu information, editable variables, and display-only variables. Screen text information comprises four text strings, one for each line of the screen, followed by a parameter which indicates whether to display an up-arrow, down-arrow, both, or neither. Arrows are used to indicate whether there are any other screens above or below the one displayed, which may be accessed by the arrow keys on the keypad.

The menu information indicates what should happen if certain keys are pressed. Any key may cause the program to go to another screen or to call a subroutine. If an arrow key is pressed, the program checks a list containing the relationships of all the screens to each other, and moves to another screen based on that information.

Editable and display-only variables are stored separately, but in the same data structure. They consist of a status byte, a pointer to where the variable's value is stored, and a screen location where the number is displayed. The status byte can indicate the length (number of digits to display) of a floating-point number, or to point to a list-type variable. List-type variables can take on any text value from a list. For example, there is a list of grain options comprising "None," "Corn," "Barley," "Wheat," and "Milo" and the like.

When the program is going to display a screen, it first finds the text information and sends it to the screen. Next, it displays the editable variables followed by the display-only variables, checking each to determine its type and branching to the correct display subroutine. Then, program control is passed to the key input processing segment.

When a key is pressed, the program determines whether it is a number. If it is, it checks the list of editable numbers to see if one of them is associated with the number pressed. If so, control is passed to the number-edit routines. For any non-number key press, or if a number was not associated with an editable number, the key is compared to the keys listed in the screen's menu information. If a match is found, either a subroutine is called or another screen is displayed, as indicated by the menu information. If no match is found, the current screen is re-displayed. In any case, the program loops back and waits for another key.

The way a number is edited depends on which type of variable it is. A floating-point number is entered directly from the keypad. When ENTER is pressed, the text number is converted to a floating-point number and stored. If CANCEL is pressed, the formerly stored number is re-displayed.

A list-type variable is edited with the up and down arrow keys. If the up arrow is pressed, the next value on the list is displayed. If the down arrow is pressed, the previous value is displayed. ENTER and CANCEL function as they do with a numeric input.

The second part of the program is the interrupt program shown in FIG. 6. Initially, samples are taken from the A/D inputs and filtered. Next, the keypad is scanned and any new key is placed in memory for the main program to retrieve. Another operation which occurs on every interrupt is turning the valve more open or more closed, depending on the current valve direction and speed. The speed of the valve is the number of interrupts out of fifteen during which it is on.

Next, the interrupt routine branches to one of fifteen different program segments. These fifteen are performed sequentially at 32.8 ms intervals and result in a complete calculation cycle time of about 0.5 seconds. This is the maximum rate of output updating. The fifteen subroutines perform the calculations, adjust the output, and perform other tasks which are necessary on a repeated basis, as shown in FIG. 6.

The output control algorithm is basically a simple proportional control, valve speed being proportional to deviation of water flow from a calculated value. However, a "predictive" algorithm is added because of the relatively slow response time of the system. This algorithm multiplies previous valve adjustment speeds with a configurable constant to predict the actual current flow rate from the signal currently present at the input. Another adjustable variable in the control algorithm is the proportionality constant between the error signal and the valve speed, allowing for the use of valves with varying sensitivities. Digital filtering for each input implements a low-pass filter given by the following difference equation:

$$y(n) = \frac{3y(n-1) + x(n)}{4}$$

where
y(n)=current output
y(n−1)=previous output
x(n)=current input

Because the system needs to respond quickly to the water-flow signal, it is filtered less heavily. The water-flow signal is simply averaged twice a second, with each average consisting of fifteen samples. Thus, it can always respond within 0.5 seconds. From the filtered inputs, the input voltage or current is calculated. Engineering units are calculated from these signal values.

Setup parameters used to make these conversions consist of two points used to define a line. For example, the voltage-to-moisture conversion parameters might be 1.0 V=9% and 2.0 V=18%. The program would interpolate (or extrapolate) linearly to calculate moisture from any voltage.

Water flow is calculated by the following formula:

$$W = \frac{G(M_T - M_I)}{100\% - M_T}$$

where W is water flow, G is grain load, $M_T$ is target moisture, and $M_I$ is incoming moisture. In practice, a conversion factor is added to the formula for water flow in units of gallons per minute; the above formula yields Cwt/min (hundreds of pound per minute), the same units used for grain flow.

Once the output is calculated and the water flow signal is available, the valve may be adjusted. First, the difference between calculated and actual flow is determined. If the calculated and actual flow are as close as the deadband (another user-adjustable parameter), no adjustment takes place. This difference is multiplied by the speed parameter and the product indicates how fast the valve should be adjusted. Thus, the greater the deviation, the faster the valve is adjusted. In reality, no real speed control is used, but the actuator is pulsed about twice per second with variable-width pulses, providing essentially the same effect.

There is also a predictive parameter which is a form of derivative-control. Because of the time required for flow to stabilize and the flow meter to respond, the controller predicts the actual flow based on flow signal and recent valve adjustments. Valve control is then based on this predicted flow rate. The predictive parameter tells the controller how heavily to factor in recent valve adjustments. Predictive decay determines how long an adjustment is remembered by the predictive algorithm. These parameters are basically set empirically by watching how much the valve tends to overshoot or undershoot, and how long it takes to reach a target flow rate.

The controller preferably includes integration software which keeps track of total grain and water flow and average grain flow, grain moisture, and water flow. Processing time is also recorded. Totals are kept for each signal, and averages are calculated every second. Average moisture calculations require totalizing the product of moisture and grain flow, and then dividing by total grain flow. Totalizing is disabled when the system is not processing grain.

The relay alarms connected with the controller are operated off of signals from the microcontroller resulting in comparisons made by the microcontroller of actual values with predetermined limits. Separate alarms can be provided to indicate grain moisture levels or grain mass flows above or below a predetermined range. An alarm can also be provided to indicate differences between calculated and actual moisture flow. The alarms can be indicated on the display and can operate to automatically shut down the conditioner apparatus or one of the operating systems thereof.

Software can be provided to work with a serial communication circuit board designed to work with the controller. The software allows one controller to act as a remote terminal for another by communicating via modem. In operation, the master does not respond to keys pressed, but sends key information to the modem. The slave unit responds to information received from the modem as if it were keys being pressed. In addition, the slave unit sends all screen information both to its screen and to the modem. The master unit does not display any of its own screen information, but sends all incoming information from the modem to its screen. In this way, the master unit acts as if it were actually the slave unit.

While in accordance with the provisions of the patent statute the preferred forms and embodiments have been illustrated and described, it will be apparent to those of ordinary skill in the art that various changes and modifications may be made without deviating from the inventive concepts set forth above.

What is claimed is:

1. A controller apparatus for a feed grain conditioner which adjusts the moisture content of feed grains to a given level, comprising
   (a) a microcontroller for receiving input signals corresponding with the moisture content of untreated grains, grain flow, and moisture flow and for processing said signals to produce output control signals;

(b) a relay driver circuit connected with said microcontroller for receiving said output control signals and for producing at least one complementary pair of actuating signals; and (c) at least one relay connected with said relay driver circuit and operable to open and close a moisture flow control valve in response to said complementary actuating signals, respectively, to control the delivery of moisture from the conditioner to the grain in accordance with said input signals.

2. A controller apparatus as defined in claim 1, and further comprising a display connected with said microcontroller to provide a visual indication of the operating parameters of the grain conditioner.

3. A controller apparatus as defined in claim 2, and further comprising a keypad connected with said microcontroller for user interface therewith.

4. A controller apparatus as defined in claim 3, and further comprising signal conditioning circuitry for filtering said input signals and calibrating the voltage and current thereof prior to delivery to said microcontroller.

5. A controller apparatus as defined in claim 4, and further comprising a plurality of relays for receiving a plurality of complementary pairs of actuating signals, one of said relays comprising an alarm.

6. A method for controlling the moisture content in feed grain as it passes through a transfer auger, comprising the steps of
(a) sensing the moisture content and mass flow of untreated grain;
(b) sensing the flow of moisture delivered to the grain;
(c) generating first input signals corresponding to the sensed moisture content, grain mass flow, and moisture flow;
(d) providing a second input signal corresponding to the type of grain passing through the auger;
(e) calculating a new moisture flow to be delivered to the grain to adjust the moisture content of the grain to a predetermined level in accordance with the first and second input signals;
(f) generating at least one pair of complementary control signals in accordance with the calculated flow;
(g) operating a moisture flow control valve in accordance with said pair of complementary control signals to increase and decrease the flow of moisture delivered to the grain, thereby to adjust its moisture content; and
(h) integrating the input signals over time to produce a plurality of output signals corresponding to the average and total grain and moisture flows and to the average moisture content of the untreated grain.

7. A method as defined in claim 6, and further comprising the step of generating a first alarm signal to indicate grain moisture levels above and below a predetermined range.

8. A method as defined in claim 7, and further comprising the step of generating a second alarm signal to indicate grain mass flow rates above and below a predetermined range.

9. A method as defined in claim 8, and further comprising the step of generating a third alarm signal to indicate differences between calculated moisture flow and actual moisture flow.

10. A method as defined in claim 9, and further comprising the step of displaying the output signals.

* * * * *